(12) United States Patent
Trinh et al.

(10) Patent No.: US 7,197,893 B2
(45) Date of Patent: Apr. 3, 2007

(54) ICE BAG COVER WITH APERTURES

(76) Inventors: Albert Long Trinh, 8671 Creekwood La., Maineville, OH (US) 45039; David Lam Trinh, 8671 Creekwood La., Maineville, OH (US) 45039

( * ) Notice: Subject to any disclaimer, the term of this patent is extended or adjusted under 35 U.S.C. 154(b) by 216 days.

(21) Appl. No.: 10/455,888

(22) Filed: Jun. 6, 2003

(65) Prior Publication Data

US 2004/0244414 A1  Dec. 9, 2004

(51) Int. Cl.
*F25D 3/08* (2006.01)
(52) U.S. Cl. ......................... 62/530; 62/457.2
(58) Field of Classification Search .................. 62/530, 62/259.3, 457.1, 457.2, 371, 430; 383/901, 383/111, 63; 607/108, 112, 114; 165/46
See application file for complete search history.

(56) References Cited

U.S. PATENT DOCUMENTS

| | | | |
|---|---|---|---|
| 2,882,692 A | 4/1959 | Robbins | |
| 2,898,744 A | 8/1959 | Robbins | |
| 2,925,719 A | 2/1960 | Robbins et al. | |
| 3,058,313 A * | 10/1962 | Robbins | 62/4 |
| 3,338,284 A | 8/1967 | Ausnit | |
| 3,643,665 A | 2/1972 | Caillouette | |
| 3,780,537 A | 12/1973 | Spencer | |
| 3,885,403 A | 5/1975 | Spencer | |
| 3,893,834 A | 7/1975 | Armstrong | |
| 4,263,079 A | 4/1981 | Sutrina et al. | |
| 4,288,891 A | 9/1981 | Boden | |
| 4,328,605 A | 5/1982 | Hutchison et al. | |
| 4,347,848 A | 9/1982 | Hubbard et al. | |
| 4,363,345 A | 12/1982 | Scheibner | |
| 4,413,481 A * | 11/1983 | Thomas | 62/371 |
| 4,453,292 A | 6/1984 | Bakker | |
| 4,523,353 A | 6/1985 | Hubbard et al. | |
| 4,527,566 A | 7/1985 | Abare | |
| 4,585,003 A | 4/1986 | Meistrell | |
| 4,622,723 A | 11/1986 | Krauss | |

(Continued)

Primary Examiner—Melvin Jones (57) ABSTRACT

Covers, articles of manufacture, and methods useful in the creation of an ice bag device that is compact, not bulky, preferably washable, optionally disposable, and which can be attached to a body part, said ice bag device comprising (a) a flexible cover open on at least one side, wherein the two edges of at least one open side and the side opposite said open side each has a row of small apertures; (b) optionally, a reclosable inner plastic container to contain cooling media such as ice, that can fit inside the outer cover, said inner container is preferably sealed on three sides and has the fourth side which is open and has a rib and groove sealing closure; (c) optionally, string like members (preferably a pair of shoelaces which are readily available in most situations) for use to attach the ice bag device to a body part and to close the open side(s) of the outer cover; and (d) optionally, a sealed plastic wrapper to keep the outer cover, the optional inner container and the optional shoelaces in a hygienic, non-contaminated condition in storage, wherein said cover, article, and/or method is optionally packaged in association with a set of instructions for use to direct the consumer how to use the product properly, to ensure that the consumer knows what benefits can be achieved, and how best to obtain these benefits, and a method of doing business in which an established entity, especially a sports organization is used to assure the user that the device and method of use are safe and effective.

20 Claims, 5 Drawing Sheets

U.S. PATENT DOCUMENTS

| | | |
|---|---|---|
| 4,669,476 A | 6/1987 | Gordon et al. |
| 4,675,948 A | 6/1987 | Bengtsson |
| 4,706,673 A | 11/1987 | Meistrell |
| 4,829,641 A | 5/1989 | Williams |
| 4,907,321 A | 3/1990 | Williams |
| 4,951,666 A | 8/1990 | Inman et al. |
| 4,964,402 A | 10/1990 | Grim et al. |
| 4,976,262 A | 12/1990 | Palmacci |
| 4,986,076 A | 1/1991 | Kirk et al. |
| 5,005,374 A | 4/1991 | Spitler |
| 5,009,828 A | 4/1991 | McCree |
| 5,045,041 A | 9/1991 | Murphy |
| 5,070,584 A | 12/1991 | Dais et al. |
| 5,074,300 A | 12/1991 | Murphy |
| 5,080,095 A | 1/1992 | Tungate |
| 5,117,823 A | 6/1992 | Weiss |
| 5,140,727 A | 8/1992 | Dais et al. |
| 5,148,804 A | 9/1992 | Hill et al. |
| 5,197,166 A | 3/1993 | Meier et al. |
| 5,215,080 A | 6/1993 | Thomas et al. |
| 5,216,900 A | 6/1993 | Jones |
| 5,545,197 A | 8/1996 | Bowen |
| 5,586,655 A * | 12/1996 | McBride .................... 206/388 |
| 5,641,325 A | 6/1997 | Delk et al. |
| 5,647,100 A | 7/1997 | Porchia et al. |
| 5,697,962 A | 12/1997 | Brink et al. |
| 5,723,002 A | 3/1998 | Delk et al. |
| 5,728,147 A | 3/1998 | Thomas |
| 5,792,213 A | 8/1998 | Bowen |
| 5,894,639 A | 4/1999 | Boden et al. |
| 5,906,438 A * | 5/1999 | Laudenberg ................ 383/63 |
| 5,934,100 A | 8/1999 | Hornick |
| 5,967,308 A | 10/1999 | Bowen |
| 5,967,579 A * | 10/1999 | Hebert ....................... 294/74 |
| 5,984,951 A | 11/1999 | Weiss et al. |
| D417,388 S | 12/1999 | Kawahara |
| 6,036,004 A | 3/2000 | Bowen |
| 6,251,131 B1 | 6/2001 | Kohout |

\* cited by examiner

ICE BAG COVER WITH APERTURES

BACKGROUND OF THE INVENTION

1. Field of the Invention

This invention relates to the general field of medical devices and/or methods for cooling injured body parts to, e.g., alleviate pain and inflammation. In particular, it relates to an improved cover for ice bags; a method of providing an ice bag device with improved availability and convenience, by the use of such cover and other readily available items for the fabrication of such ice bag device, e.g., when needed; and the secure attachment of the ice bag to an injured body part, such as a limb or body trunk. It also relates to an article of manufacture that provides such cover, to the method of fabricating and/or using such ice bag device using such cover; to the provision with the cover of instructions for use that aid unskilled users to provide effective emergency assistance ("first aid treatment") to injured body parts, and to methods of doing business that promote the availability of such covers, articles of manufacture, and methods, etc., to many more people who may need such first aid treatment.

2. Description of the Related Art

The desirability of using ice bags for thermal therapy is well accepted. Ice bags enable the user to apply cold to an injury such as a bruise or sprain without unacceptable mess. A common ice bag that is commercially available is the reusable type comprising a water-impermeable, commonly a rubber-lined, flexible bag having a tubular rigid neck and a removable cap. To use, the bag is filled with ice cubes or ice chips and closed with the cap, then the bag is applied to the bruised body part and held in place by hand.

Another type of cold pack that is commercially available is a refrigeratable gel cold pack which comprises a refrigerant or coolant gel material contained in a plastic housing which can be either flexible or relatively inflexible. By "refrigeratable" it is meant that the gel can be cooled by placing the gel in a refrigerator, used as the coolant in an ice bag, and then cooled again for a subsequent use. The gel packs are stored in a freezer for chilling or cooling and are then ready for use. Also commercially available is a chemical pack which comprises two or more pouches for separately storing chemical reactants which can be mixed to produce an endothermic cooling mixture.

A common home-use ice bag can be made using a commercially available reclosable plastic sandwich or freezer bag with a zipper seal, such as a Ziploc™ plastic bag filled with ice (Ziploc is a registered trademark of Dow Chemical Company, Midland, Mich.). By "reclosable" it is meant that the bag can be opened and closed numerous times.

One of the disadvantages of these ice bags is that they need to be inconveniently held by hand to maintain contact with the injured body part. To overcome this inconvenience, several types of ice bag devices comprising a holder for these ice bags have been created. These ice bag devices can be strapped around a body part, with, e.g., loop and hook mating Velcro™-type fastening straps. These ice bag devices are usually of complicated design, large and bulky in size and/or expensive to produce and/or difficult to be washed for reuse.

Thus, there is a need for an improved, inexpensive and readily available ice bag device that can be used without having to be held by hand. Youth contact sport activities such as soccer, football and basketball are more and more popular. Unavoidably, some occasional bruises and injuries such as sprains accompany these activities. There is a need for an inexpensive and readily available ice bag device for such events. Such ice bag needs to be attachable to a body part, such as a limb or body trunk or head, because the injured player would likely prefer to stay to watch until the end of the game, but does not want to hold the ice bag with his or her hand for the duration of the game. Applying the ice bag device by hand not only is inconvenient, but it also can restrict the mobility if the injury is, e.g., in a lower part of the body such as in the leg or foot, and it can be awkward if the injury is, e.g., in a hard to reach body part such as on the back. It is also preferred that the cold should not reduce the skin temperature excessively since that can cause damage, e.g., frostbite. Such ice bag is preferably easily washable for reuse, or optionally disposable, because it is most likely applied to an unwashed and likely sweaty body part. Injuries that need an ice bag treatment also can happen in other types of outdoor activity such as picnicking, hiking and other outings, and/or on trips. Such ice bag device needs to be compact, not bulky, so that preferably it can fit in a first-aid box along with other first-aid items. Preferably such ice bag device is easily manufactured and used.

SUMMARY OF THE INVENTION

This invention relates to, alternatively: (A) a flexible ice bag outer cover having at least one open end or side that is optionally capable of being sealed, and having dimensions suitable to contain one or more inner cooling packs or inner "cooling bags", hereinafter "pack" or "packs", wherein each said cooling pack can comprise a generally liquid impermeable container containing cooling media that can be inserted into said outer cover through said open end, and wherein said outer cover has a plurality of small apertures, wherein "plurality" is typically from 1 to about 40, preferably from about 2 to about 20, and more preferably from about 4 to about 10 small apertures, to permit the insertion of one, or more separate, string-like, members that can be used to attach the ice bag device, when it is assembled and filled with at least one cooling pack, to an injured body part of the user; and optionally, but preferably, to permit lacing one of the string-like members through the small apertures in both sides of the bag near the open end of the outer cover to close said open end; (B) a method of creating an ice bag device using said outer cover (A) by (1) filling a fluid impermeable container, preferably a plastic bag sealable by interlocking rib and groove sealing closure, with a cooling medium, typically ice or an ice and water combination, either before or after (2) inserting the fluid impermeable container into the said outer cover, (3) optionally, but highly preferably, sealing said outer cover, preferably by lacing one or more string like members, typically shoelaces or bootlaces, through said small apertures, and then (4) using the ends of said string like members to attach the completed ice bag device to the said injured body part; or, alternatively, a method of using shoelaces or bootlaces to attach an ice bag device having a cover that has a series of small apertures, to a body part, and/or to close an opening of the cover of said ice bag device by lacing said shoelaces through said apertures; (C) the completed ice bag device prepared by the said method; (D) the association of instructions for the said method with said cover to ensure that the method can be practiced efficiently, quickly, and effectively so as to maximize the effect of the cooling treatment on an injury; (E) an article of manufacture comprising the following elements: (1) one or more outer covers (A), (2) optionally one or more empty resealable fluid impermeable plastic zipper container(s) or one or more sealed fluid impermeable containers containing a cooling medium such as a cooling gel or an endothermic chemical cooling system, (3) optionally two or more shoestring like members, (4) optionally a sealed plastic film wrapper to contain and keep one or more of said elements in a hygienic, non-contaminated condition in storage, and (5) optionally packaged in association with instructions (D); and (F) the method of doing business wherein one or more of the cover (A), the method (B), the article (E), and/or set of instructions (D) are distributed with the approval of one or more organizations or entities having an association with individuals that are likely to be injured and thus need an ice bag device on an urgent basis, such as an amateur or professional athletic association, so as to maximize the availability and acceptance of the said cover, method, and/or article, where they are needed and/or to provide assurance that the method, device, instructions, etc. are effective and safe. The cover and the ice bag are compact, not bulky, preferably washable, optionally disposable, and can be attached to a human and/or animal body part, such as a limb or body trunk.

DETAILED DESCRIPTION OF THE INVENTION

In one aspect of this invention there is provided a flexible outer cover for an ice bag or cold pack. The flexible outer cover is preferably a unitary structure, typically either a sack structure (or pouch structure) with one open end or side, or a generally tubular structure with two open ends, that has rows of small apertures that permit string like members, typically shoestrings or shoelaces, to be threaded, or laced, or woven, through the apertures and then tied to attach the ice bag device to an injured body part of the user, and optionally but preferably to close the open end(s) or open side(s) of the outer cover. The outer cover is preferably rectangular or square in shape, or configuration, when flattened, said outer cover preferably having three closed (sealed) edges (two vertical and one lateral sides) and an opening on one lateral side, wherein the two sides of the outer cover that form the opening on the open lateral side and the edge of the closed lateral side opposite to the open side each has a row of n small apertures, with n being preferably an even number, more preferably being 2, 4, 6, 8 or 10, even more preferably 4 or 6, most preferably 4, and wherein said rows are preferably close to the edges of the lateral sides and parallel with the edges, and wherein said outer cover preferably has one or more vertical compartments.

As used herein, "aperture" can be, e.g., a small incision, a metallic or plastic eyelet, a buttonhole, a loop, a "tube", or any similar structure that can at least partially surround the string like members to maintain the cover in position. Small incisions can be used, but normally require some reinforcing of the edges to prevent tearing, raveling, etc. I.e., the incision becomes a buttonhole when the reinforcement is a thread sewn around the incision and an eyelet when the reinforcement is metal, plastic, etc. The aperture can also be formed from a material that is different from the cover and attached to the cover, e.g., a loop of some suitable material like string, fabric, metal, plastic, etc. Similarly, a portion of the cover can be formed into a loop or tube and then sealed by sewing, glue, staples, etc. The aperture is preferably not a long tube, since such structures make it difficult to rapidly thread the string like members through the tube. "Clips" can also be used to form the apertures and attach the string like members to the cover. Clips are not preferred since they add to the complexity of fabrication and typically add to the weight. Furthermore, if the clips bind the string like member, it is more difficult to position the ice bag device. Simple incisions that have the edges reinforced are preferred. Since the ice bag device has at least a limited ability to slide along the string like member after it is threaded through the small apertures, it is relatively easy to position the ice bag device after the ends of the string like members are tied to attach the ice bag device to the body.

The outer cover is made at least partly of a relatively flexible substrate. The flexible substrate is typically a fabric, normally woven and/or non-woven and/or knitted, but can also be a resilient foam sheet. The outer cover can be made of material such as, but not limited to, woven, knitted, crocheted, or non-woven fabric of natural and/or synthetic fibers such as cotton, polyester, nylon, acrylic, rayon, and the like, felt, velvet, flocked material, heat-bonded plastic fiber material, such as, melt-blown, spun-bonded polyethylene or polypropylene, carded thermo-bonded polypropylene and rayon blend, solvent-laid thermally bonded polypropylene (e.g., Tyvek™ by Dupont), resilient open-cell or close-cell plastic foam, porous and nonporous plastic film and/or rubber, paper, laminated materials such as laminate of rubber and non-woven layers, and the like. It is also permissible to have the outer cover be water impermeable and sealable to eliminate the need for the inner cooling pack. However, the different requirements for the outer cover and the inner pack make it highly preferable to provide both the outer cover and the inner pack. It is easier to wash the outer cover when it is fabric and it is easier to fabricate when there is no need to have it water impermeable.

The edges of the outer cover can be sealed by sewing, gluing, heat sealing, and the like or can be integral, e.g., when formed from tubular material that requires no sealing on the side (vertical) edges. The preferred material makes the outer cover of the ice bag flexible, conformable, and optionally stretchable, at least on the side that is in contact with the body. The material that contacts the body also preferably slows the cooling of the body part to avoid damage by overcooling, e.g., frostbite. However, the material should allow heat to flow from the injured body part. Optionally, the cover can comprise additional flaps that can be placed between the cooling pack and the injury. The desired effect is cooling without freezing and the cooling is preferably at a rate that produces no more pain than can be withstood by the user and which does not cause damage to the treated area.

The outer cover can most conveniently have one compartment designed to have dimensions suitable to hold one inner cooling pack comprising an at least relatively liquid (e.g., water, brine solution, or gel) impermeable inner container that contains a cooling medium, wherein said inner container is preferably and conveniently either a commercially available reclosable "zipper" or "zip lock" bag such as a food, e.g., sandwich, snack, or freezer zipper bag, as described hereinafter, or a specially made inner container of any suitable size and thickness. The outer cover can also be divided into two or more compartments, preferably vertical compartments, to hold two or more inner cooling packs. The preferred multi-compartment outer cover has two or three compartments, more preferably two compartments, especially for compact size inner packs. By "vertical compartment", it is meant that the compartment has two vertical closed sides and at least one lateral open side that can be closed, e.g., by use of a shoelace. An ice bag device of the present invention comprising an outer cover having multiple compartments to contain two or more inner cooling packs has the advantage of distributing solid cooling media such as ice chips or ice cubes more evenly on the skin surface, and better preventing the ice chips or ice cubes from accumulating into one area, thus providing more even cooling and/or comfort.

The outer cover can be conveniently separated into two or more compartments, preferably of approximately equal size, by vertical sewn lines, glue lines or staple lines that are stitched or otherwise added into the outer cover. Preferably the compartment(s) have dimensions that can accommodate/ fit the reclosable inner cooling packs comprising commercially available plastic zipper containers of the quart size or sandwich size as described hereinafter. A preferred multi-compartment outer cover has compartments of a size that is suitable to hold plastic zipper containers that are commercially available snack or sandwich bags, as described hereinafter. The outer cover that has one compartment can have larger vertical or lateral sides. In a preferred embodiment, the outer cover with one compartment has the lateral open side larger than the vertical closed side. Conversely, in another embodiment, the outer cover having more than one compartment preferably has each compartment with the lateral open side smaller than the vertical closed side. These preferred configurations are based upon the use of zipper bags with normal dimensions.

Another aspect of this invention relates to an ice bag device that can be attached to a human and/or animal body part, such as a limb or body trunk, said ice bag device comprising:

(a) an outer cover as described hereinabove;

(b) one or more preferably reclosable, liquid impermeable, inner, preferably plastic, containers, preferably rectangular or square in shape, to contain cooling media such as ice, e.g., cubes, ice chips, crushed ice, or ice and water combination, to form one or more cooling packs that can fit inside the compartment(s) of the outer cover, each inner container is preferably closed, e.g., sealed, on three sides and has the fourth side open, preferably having a reclosable closure, more preferably a rib and groove zipper closure; and (c) a pair of loose (unattached) strings, preferably a pair of shoelaces or shoestrings preferably having narrow and hardened tips and preferably with flat body, that can be threaded, or laced, through the rows of small apertures of the outer cover to attach the ice bag device to a body part and, optionally but highly preferably to close the open side of the outer cover and then tied;

and wherein the ice-filled inner pack(s) of (b) can optionally be replaced by chilled or frozen refrigeratable gel pack(s) and/or endothermic chemical cold pack(s), when said pack(s) are available.

In particular, this invention relates to an assemblage of elements, comprising an outer cover as described hereinabove and one or more zipper bags, and a pair of shoelaces, that can be used to create an ice bag device, that is compact, e.g., can fit in a first-aid box along with other first-aid items, to be used at home or away from home, e.g., in sporting events, such as at a soccer field or basketball court, in other outings such as hikes or picnics, and/or on trips. Such ice bag device is preferably easily manufactured and/or inexpensive.

The inner container is preferably constructed of a liquid impermeable, e.g., waterproof, synthetic "plastic" material such as a polyethylene film. Such inner bag is preferably closed (e.g., sealed or an integral structure) on three sides and has the fourth side that is open but that preferably has a reclosable zipper closure, preferably an interlocking rib and groove, or male and female sealing closure, as described, e.g., in U.S. Pat. No. 3,338,284 issued Aug. 29, 1967 to Ausnit; U.S. Pat. No. 4,263,079 issued Apr. 21, 1981 to Sutrina et al.; U.S. Pat. No. 4,363,345 issued Dec. 14, 1982 to Scheibner; U.S. Pat. No. 4,829,641 issued May 16, 1989 and U.S. Pat. No. 4,907,321 issued Mar. 13, 1990, both to Williams; U.S. Pat. No. 5,009,828 issued Apr. 23, 1991 to McCree; U.S. Pat. No. 5,070,584 issued Dec. 10, 1991 to Dais et al.; U.S. Pat. No. 5,140,727 issued Aug. 25, 1992 to Dais et al.; U.S. Pat. No. 5,647,100 issued Jul. 15, 1997 to Porchia et al.; and the references cited therein.

Preferred inner containers are rectangular or square in shape. Each inner container can be defined by two sets of dimensions, namely, the outer dimension that includes the sealing closure line or part, and the inner dimension that counts only the storage area, without the sealing closure part. Each dimension is typically defined by two sides, the first side is a lateral or opening side and the second side is a vertical closed side. In use, the inner container(s) can be filled with, e.g., ice cubes, ice chips, crushed ice, or ice and water mixture, then the reclosable zipper closure is firmly pressed along the sealing closure line in order to hermetically seal the inner container(s). Preferably the sealing closure part is folded back onto one side of the inner bag before the inner bag is placed in a compartment of the outer cover, in order to maximize the cold contact surface and/or to better maintain the seal against any accidental opening due to pressure applied on the side of the ice bag device.

Preferred reclosable inner containers for use in the ice bag device of the present invention are the commercially available household reclosable plastic zipper bags for use as food containers or freezer storage bags, and sold, e.g., under the brand names Ziploc® or Glad®, or store name, e.g., Kroger®, and the like. The preferred commercially available household bags for use in an outer cover that has one compartment are the quart size bags (typically having an outer dimension of from about 17 cm×21.5 cm to about 18.5 cm×23 cm, and an inner dimension of from about 17 cm×19.5 cm to about 18.5 cm×21 cm) or the sandwich bags (typically having an outer dimension of from about 16 cm×18.5 cm to about 17 cm×18.5 cm, and an inner dimension of from about 16 cm×14 cm to about 17.5 cm×16 cm). The preferred commercially available household bags for use in an outer cover that has more than one compartment are the sandwich bags (typically having an outer dimension of from about 16 cm×18.5 cm to about 17 cm×18.5 cm, and an inner dimension of from about 16 cm×14 cm to about 17.5 cm×16 cm) or the snack size bags (typically having an outer dimension of from about 16 cm×9 cm to about 17 cm×11.5 cm, and an inner dimension of from about 16 cm×7.5 cm to about 17 cm×9 cm). Industrial zipper bags of many sizes are also available, e.g., from Lab Safety Supply, Inc., Janesville, Wis.

The inner zipper containers can be made of plastic film, preferably transparent plastic film. One common material used in the household and industrial zipper bag is polyethylene. The zipper bags that are useful as inner containers of the present invention typically have a film thickness of from about 0.01 mm to about 0.25 mm, preferably from about 0.02 mm to about 0.15 mm, more preferably from about 0.02 mm to about 0.1 mm, and even more preferably from about 0.03 mm to about 0.08 mm.

When the inner bag has the vertical side longer than the lateral side with the zipper closure, such as the case of most quart size bags, or when the inner bag has two sides having approximately the same length, such as some sandwich bags, it is preferred to place the inner bag in a compartment such that the lateral side with the zipper closure is at the same side as the lateral open side of the outer cover compartment. When the inner bag has the vertical side significantly shorter than the lateral side with the closure, such as in the case of the snack size bags, or some sandwich bags, it is preferred to place the inner bag in a compartment such that the lateral side with the sealing closure is at the same side as the vertical closed side of the outer cover compartment.

In a preferred embodiment, specially made elongated inner bags are used in compact ice bag devices with a smaller outer cover having two or more compartments. For the inner bag, "elongated" means that the inner bag has the lateral open side (with reclosable closure) that is smaller than the vertical closed sides. Thus, a non-limiting example of a preferred ice bag device comprises elongated inner bags having an outer dimension of from about 8 cm×18 cm to about 12 cm×20 cm and an inner dimension of from about 8 cm×18 cm to about 16 cm×18 cm, and an outer cover having two or three compartments that can accommodate the selected inner bag size, along with the optional shoelaces and optional outside plastic wrapper.

The ice in the inner cooling pack can be ice chips, but is preferably in the form of small pieces, e.g., pieces having a maximum dimension of at least about 1 cm, preferably at least about 2 cm, more preferably at least about 3 cm and less than about 10 cm, preferably less than about 8 cm, more preferably less than about 7 cm. Although the ice will not be in contact with the skin, it is highly preferred that the ice be hygienic and potable.

The outer cover can optionally be used to hold and apply other cold media in place of the ice-filled inner cooling pack. Non-limiting examples of such cold media include a pre-cooled gel pack, or a chemical cold pack. A cold gel pack is a refrigeratable gel cold pack that comprises a refrigerant or coolant gel material contained in a permanently sealed plastic housing which can be either flexible or relatively inflexible. The gel packs are stored in, e.g., a conventional household freezer for chilling or cooling and are then ready for use. Non-limiting examples of cold gel packs and/or coolant compositions are given in U.S. Pat. No. 3,780,537 issued Dec. 25, 1973 and U.S. Pat. No. 3,885,403 issued May 27, 1975, both to Spencer, and U.S. Pat. No. 5,148,804 issued Sep. 22, 1992 to Hill et al. Many commercially available gel packs, such as the Nexcare™ First Aid Reusable Cold Pack produced by 3M Health Care, St. Paul, Minn., Ace® Brand Cold Compress Reusable and Ace Brand Hot & Cold Compress Reusable distributed by BD Consumer Healthcare, Franklin Lakes, N.J., are elongated in dimension with sizes of from about 23 cm×9.5 cm to about 27 cm×12.5 cm. When they are stored in a household freezer, they are chilled but not frozen. They can be folded in two in order to be placed in a compact outer cover with one compartment of the present invention that is designed to accommodate one sandwich zipper bag. Preferably they can be used in an elongated outer cover that is designed to accommodate the elongated gel packs, with the open side of the outer cover being a long side having rows of small apertures as described hereinbefore, each row preferably comprising from about 6 to about 10 apertures. The permanently sealed plastic container can also contain liquid water to be placed in, e.g., a freezer to form ice for use in the method and/or article of the present invention. The frozen ice contained in such permanently sealed plastic container adopts the shape of the container and has the dimension of such container, including, optionally, dimensions larger than about 10 cm.

A chemical cold pack typically comprises an endothermic chemical system comprising different chemicals which, when mixed together, undergo an endothermic reaction to reduce the temperature of the cold pack. Typically, the different chemicals are contained in separate compartments to prevent a premature reaction. The chemical cold pack is "activated" when the compartments are, e.g., connected by a certain means so that the chemicals are mixed to produce the endothermic reaction. An example of such endothermic chemical system is dry ammonium nitrate and water. Other non-limiting examples of endothermic chemical systems and/or chemical cold packs are given in U.S. Pat. No. 2,882,692 issued Apr. 21, 1959, U.S. Pat. No. 2,898,744 issued Aug. 11, 1959, U.S. Pat. No. 3,058,313 issued Oct. 16, 1962, all to Robbins; U.S. Pat. No. 2,925,719 issued Feb. 23, 1960, to Robbins et al.; U.S. Pat. No. 3,643,665 issued Feb. 22, 1972 to Caillouette; U.S. Pat. No. 3,893,834 issued Jul. 8, 1975 to Armstrong; U.S. Pat. No. 4,986,076 issued Jan. 22, 1991 to Kirk et al.; and U.S. Pat. No. 5,545,197 issued Aug. 13, 1996, U.S. Pat. No. 5,792,213 issued Aug. 11, 1998, U.S. Pat. No. 5,967,308 issued Oct. 19, 1999, and U.S. Pat. No. 6,036,004 issued Mar. 14, 2000, all to Bowen.

The optional pair of loose, unattached strings, preferably loose shoelaces or shoestrings, bootlaces, and/or draw cords, can be constructed with materials such as natural and/or synthetic fibers, fabric, leather, and the like. By loose shoestrings, it is meant the shoestrings, or shoelaces, or bootlaces, are free, separate, or are removed from the shoes, and no longer laced and/or attached to the shoes when used for the purpose of the present invention. By draw cord, it is meant a string or cord that is used to tie a hood or waistband on sweat suits, swimsuits, athletic or casual clothes, and the like.

The preferred strings for use in the present invention are shoestrings or shoelaces or bootlaces, having at least one hardened and preferably narrow tip, preferably two hardened and narrow tips at both ends of said shoestrings, wherein said hardened narrow tip is preferably from about 0.5 cm to about 2 cm, more preferably from about 1 cm to about 1.5 cm in length. Some shoestrings such as some leather strings are inherently stiff and do not need to be hardened further. However, most shoelaces made of natural and/or synthetic fibers need to have the tips narrowed and hardened for easy lacing through the rows of small apertures of the outer cover. Most commonly, the shoelace tips are made narrow and hardened by being compressed and encased by a round or oval hard plastic or metallic tube. The ends of the laces can also be hardened, e.g., by dipping said ends into a hot melt resin that hardens upon cooling. Alternatively, small pieces of adhesive tape can be wrapped around one, or both ends to provide hardened tips. One end of a band-aid can be used for this purpose.

The hardened and narrow tips of the shoestrings make it easy for the strings to be laced through the rows of small apertures of the outer cover. Thin fabrics can also be sewn into long strings and provided with hardened tips. Thick sheets of leather can be cut into thin, long strips to form shoestrings that are sturdy and often do not need to be strengthened at the tips for lacing. Preferably shoestrings have a length of from about 0.25 meter (about 10 inches) to about 2 meters (about 80 inches), more preferably from about 0.5 meter (about 20 inches) to about 1.5 meters (about 60 inches). Any type of shoestring can be used in the present invention, such as round or flat, or oval with two side edges, but the flat and thick sport shoelaces or shoestrings are preferred because they are more comfortable to the wearer of the ice bag device of the present invention. Such flat shoelaces spread the force needed to keep the ice bag device in place over a wider area, resulting in a lower pressure on the skin.

A string, e.g., a shoestring that is laced through the two rows of small apertures of the open side of the outer cover serves both as a closure for that open side and to attach the ice bag device to the body part. Thus, the need for a separate closing mechanism for the opening of the ice bag outer covers, commonly with the use of the expensive Velcro strips, as described as closures for other ice bags of the art, is rendered unnecessary. It is surprising that when a pair of shoestrings of the present invention are used to attach the ice bag device to a body part, the strings can be tied rather loosely and do not need to be tied really tightly but can still keep the ice bag device securely in place, while at the same time avoiding a constriction that can adversely affect blood flow.

In another embodiment, the ice bag device of the present invention can additionally comprise a pair of cord locks to provide a quick tying of the shoelaces and an easy adjustment of the strapping of the ice bag around a body part. A cord lock in this invention is meant a device in which the two ends of a string are extended through a passage in a body of the device, and are adapted to be releasably locked against longitudinal movement by, e.g., a movable slide element positioned within the body. Non-limiting examples of cord locks that are suitable for use with the ice bag device of the present invention are those disclosed, e.g., in U.S. Pat. No. 4,288,891 issued Sep. 15, 1981 to Boden, U.S. Pat. No. 4,328,605 issued May 11, 1982 to Hutchison et al., U.S. Pat. No. 4,453,292 issued Jun. 12, 1984 to Bakker, U.S. Pat. No. 4,675,948 issued Jun. 30, 1987 to Bengtsson, U.S. Pat. No. 4,986,076 issued Nov. 18, 1986 to Krauss, U.S. Pat. No. 5,197,166 issued Mar. 30, 1993 to Meier et al., U.S. Pat. No. 5,894,639 issued Apr. 20, 1999 to Boden et al., Des. 417,388 issued Dec. 7, 1999 to Kawahara, and references cited therein, said patents being incorporated herein by reference.

In another embodiment, the pair of shoelaces can be threaded into the rows of small apertures of the outer cover (after the outer cover has received the ice-filled inner bag(s)) to close the open end of the outer cover, and then tied into a pair of loops that serve as convenient holders of the ice bag device, if the injured person prefers to hold the ice bag device by hand to apply the ice bag device to the injury. This can be desirable if the cold causes pain when applied to the skin for longer times. Having a means for holding the ice bag without being in contact with the cold media avoids excessive cooling of the hand and thus helps ensure that the ice bag is used for a sufficient period of time to provide a benefit.

In an alternative embodiment, this invention relates to a flexible, liquid impermeable outer cover with a unitary structure to contain ice, as described herein above, but wherein the outer cover layer and the inner container layer are laminated together, said cover preferably having a sack structure with three closed sides and one open side (or open end), wherein the open side, or sides if more than one side is open, is sealable by a leak-proof zipper closure to retain the ice, and wherein the open side and the closed side opposite to the open side have extended peripheries having rows of small apertures that permit shoelaces to be threaded through to attach the ice-filled cover to an injured body part of the user. The wall of the cover is preferably made of laminated materials such as laminates of plastic and woven or non-woven fabric layers, with the plastic layer providing the liquid impermeability and the construction of the zipper closure and the fabric layer providing a degree of insulation to slow the cooling of the treated body part, to avoid damage by overcooling, e.g., frostbite. Such unitary structures are more difficult to manufacture.

The present invention also relates to a method of using loose shoelaces or shoestrings to attach an ice bag device having small apertures, to a body part, and/or to close the opening of the outer cover of said ice bag device. This method is of great value, since it permits one to carry/store only the described outer cover, optionally with one or more empty zipper bag containers, as separate item(s), yet permitting the fabrication and use of an ice bag device readily and immediately when it is needed. Shoelaces are normally available, especially at sporting events, and they have ends that can be readily threaded through small apertures. They also typically have flat sides that keep the ice bag device in place without excessive pressure.

The present invention also relates to an article of manufacture comprising one or more outer covers of the present invention, and optionally at least one other element which is: one or more empty reclosable plastic zipper containers, or one or more sealed, fluid impermeable plastic containers containing water, refrigeratable cooling gel, or endothermic chemical cooling system, preferably one or more empty reclosable plastic zipper containers, to contain cooling media, that can fit inside the enclosure of the outer cover; two or more shoelaces; and/or a sealed plastic film wrapper to contain and keep said outer cover, said optional inner zipper containers, and said optional shoelaces in a hygienic, non-contaminated condition in storage; and/or wherein said article is optionally, but preferably, packaged in association with a set of instructions for use to direct the consumer how to use the cover to assemble an ice bag device, how to use the product properly, and to ensure that the consumer knows what benefits can be achieved, and how best to obtain these benefits. The sealed plastic wrapper is useful to keep the elements of the ice bag device in a hygienic, non-contaminated condition in storage and/or to prevent accidental loss of one or more of the elements. The plastic wrapper can be transparent or opaque, and can be white or colored. Preferably the plastic wrapper is transparent or marked with the contents so that the article can be readily identified in an emergency.

The present invention also relates to the association of instructions for use with the outer cover, the ice bag device, the method, or the article of manufacture described hereinabove to ensure that the method can be practiced and the cover and/or the article be used efficiently, quickly, and effectively so as to maximize the effect of the cooling treatment on an injury. The set of instructions provides the information on how to use the outer cover, the inner containers, the shoelaces, and the cooling media such as ice, as well as the cooling gel or the chemical cooling pack, to create a convenient ice bag device that provides immediate cooling to an injury.

The set of instructions provides the information on how to use the outer cover, the shoelaces that are either provided with the package or readily obtained from a pair of shoes or boots, liquid impermeable inner containers, and cooling media such as ice to create a convenient ice bag device that provides immediate cooling to an injury.

The set of instructions of the present invention preferably includes one or more of the following instructions: to direct the consumer to first fill the inner zipper container(s) with cooling media such as ice cubes, ice chips or crushed ice, then to seal the filled inner container(s), then, optionally, but preferably, to fold the sealing zipper closure back against one side of the inner zipper bag, then to place the filled inner ice pack(s) or ice bag(s) in the compartment(s) of the outer cover, then to lace the rows of small apertures of the two sides of the outer cover with a pair of shoelaces, or other string like structures, that are either provided with the ice bag device or removed, e.g., from a pair of shoes, and/or to apply the resulting ice bag device over the injured part by attaching the ice bag device to the body part by tying the ends of the pair of shoelaces.

The set of instructions can include an instruction to direct the consumer to a source of ice or cold fluid, preferably including a home refrigerator, ice boxes or ice coolers for beverages at a sport game, and/or a fast food restaurant and/or hotel or motel when one is on a trip. There is usually some ice or cold fluid, e.g., water or other chilled drink, available at sporting events.

The set of instructions can include an instruction to direct the consumer to optionally use already cooled gel pack(s) or endothermic chemical cooling pack(s) in the place of the ice-filled inner cooling pack(s).

The set of instructions can also include an instruction to direct the consumer to tie two or more short shoelaces together to form a longer string for a large body part, or when long shoelaces are not available. These instructions can also advise the consumer to thread part of each shoelace through the openings before tying if the openings are too small to allow a knot to pass. The set of instructions can have an instruction to inform the consumer of the option of threading the shoelaces into the rows of small apertures of the outer cover, after the outer cover has received the ice-filled inner bag, and tying them into a pair of loops that serve as convenient holders of the ice bag device to hold the ice bag device by hand to apply to the injury.

The set of instructions can also include an instruction to direct the consumer to keep the article of the present invention readily available, e.g., in their first-aid kit. In order to cool the injured body part, the instructions can suggest initially contacting the injured part directly with the cooling pack followed by attaching the completed ice bag to the clothing to minimize the danger of overcooling the flesh during a prolonged application. The set of instructions preferably comprises one or more of the hereinabove instructions.

To keep the compact size, in a preferred embodiment, the article of manufacture and/or the ice bag device kit of the present invention can comprise a pair of temporary, short shoestrings, typically from about 0.3 to about 0.6 meter in length. In this case, the set of instructions for use will preferably include an instruction or suggestion to direct the consumer to remove a longer pair of shoelaces that are usually available from a pair of unworn shoes, or from the pair of shoes or boots that are being worn by the injured person or another person, and use them to attach the ice bag device to a body part, while the provided shorter pair of shoestrings is used for temporarily tying the shoes or boots.

The set of instructions can be printed, e.g., on one or more of: the package, the wrapper, an accompanying instruction flyer or booklet, and/or communicated via print and/or electronic mass media, e.g., newspapers, magazines, radio, television, internet, circulars, etc., to members of sport and/or outdoor organizations, and the like.

The instructions can be in one or more languages. The instructions can be in words, or illustrative images and/or icons preferably in combination with words. It is preferable to have the instructions contain pictorial representations of the steps in preparing and using the ice bag device to supplement, or replace the written instructions when the user is not familiar with the language(s) of the instructions.

This invention further relates to an outer cover, an ice bag device and/or an article of manufacture comprising said outer cover and other elements of the ice bag device of the present invention, wherein one or more of the outer cover, the inner container(s), the wrapper, the package, and/or the set of instructions carry indicia showing, e.g., a logo, emblem, symbol, motif, sign, figure, mark, icon, pictogram, insignia, design, image, description, and/or advertisement for, e.g., a sport league, sport franchise, sport sponsor, non-profit or governmental organization, and/or for-profit commercial or industrial organization. The use of such indicia provides a measure of assurance to the user that the device is useful and not harmful, especially when the instructions are followed.

The above use of indicia can be used as part of the method of doing business in which the use of the outer cover, the article, etc., are promoted by using one or more existing associations, businesses, etc., to make, distribute, sell, or recommend the ice bag article, the outer cover, and/or the method, to provide assurance to the intended user that the device is acceptable for the intended result. Since the primary benefit of the invention is to obtain fast treatment of trauma to diminish the damage to the individual, it follows that the user will normally not be a medical professional, and often will not have even basic first aid skills. It is important that these individuals know that the ice bag device is safe and effective and that the instructions are safe when followed, and that the individuals have access to basic instructions for use.

This invention relates to a method of doing business wherein the outer cover, other elements of the ice bag device and/or the article of manufacture comprising said outer cover and other elements of the ice bag device of the present invention, are distributed with the approval of one or more entities having an association with individuals that are likely to be injured and need an ice bag device on an urgent basis, such as an amateur or professional athletic association and/or optionally, attaching the indicia of at least one of said entities to said article and/or associating said indicia with said article.

Specific embodiments are described hereinafter with reference to the drawings.

Figures 1, 2, 3:
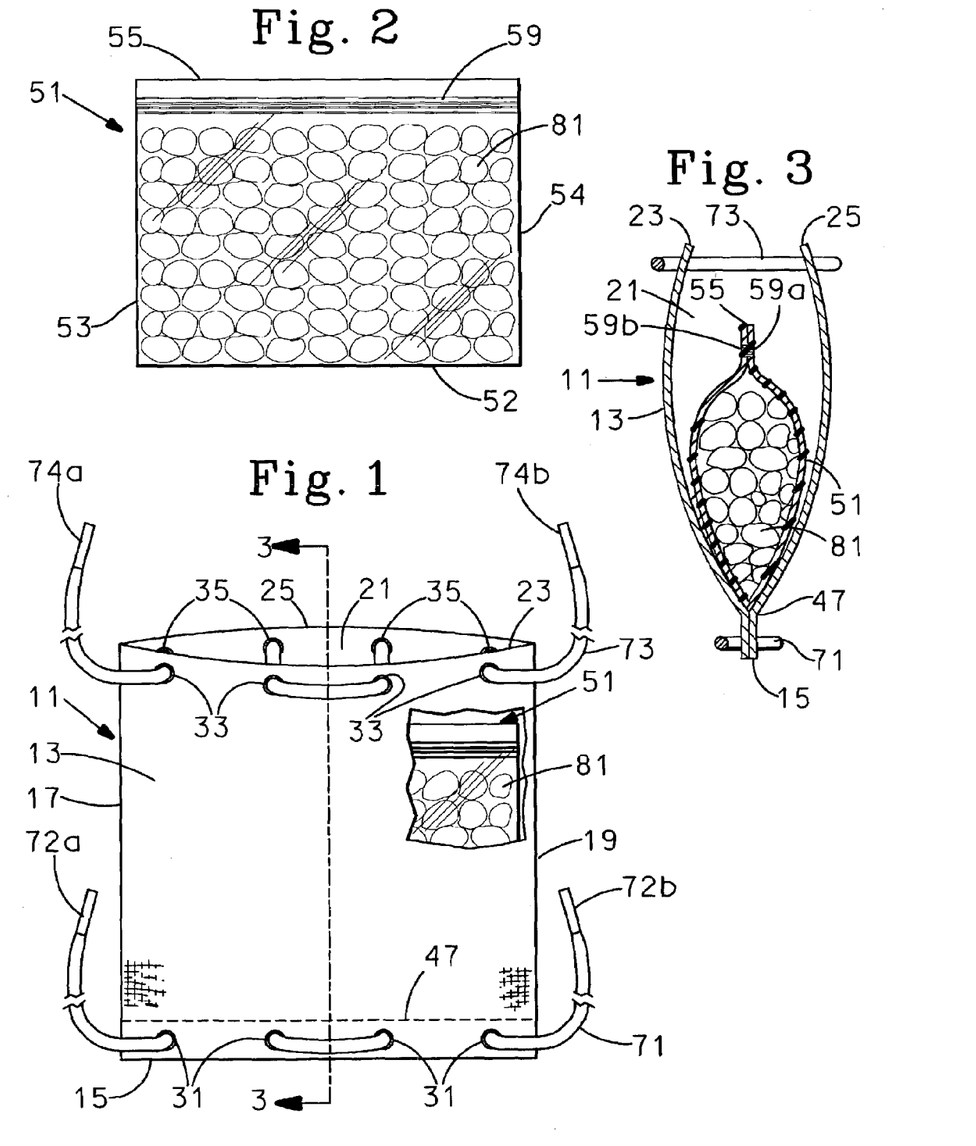
FIG. 1 is a perspective view of an ice bag device of the present invention showing an outer cover with one compartment, said outer cover is partly cut away to better show an inner plastic zipper bag filled with ice chips, and with a shoestring laced in the row of small apertures at the lateral bottom side of the outer cover, and another shoestring laced in a pair of rows of small apertures at the two top edges that form the open top lateral side of the outer cover.
FIG. 2 is a plan view of the isolated zipper bag filled with ice chips of the ice bag device of FIG. 1.
FIG. 3 is a side, cross-sectional view of the ice bag device of FIG. 1 comprising the outer cover containing an inner container filled with ice chips taken along the line 3—3.
Figures 11, 12:
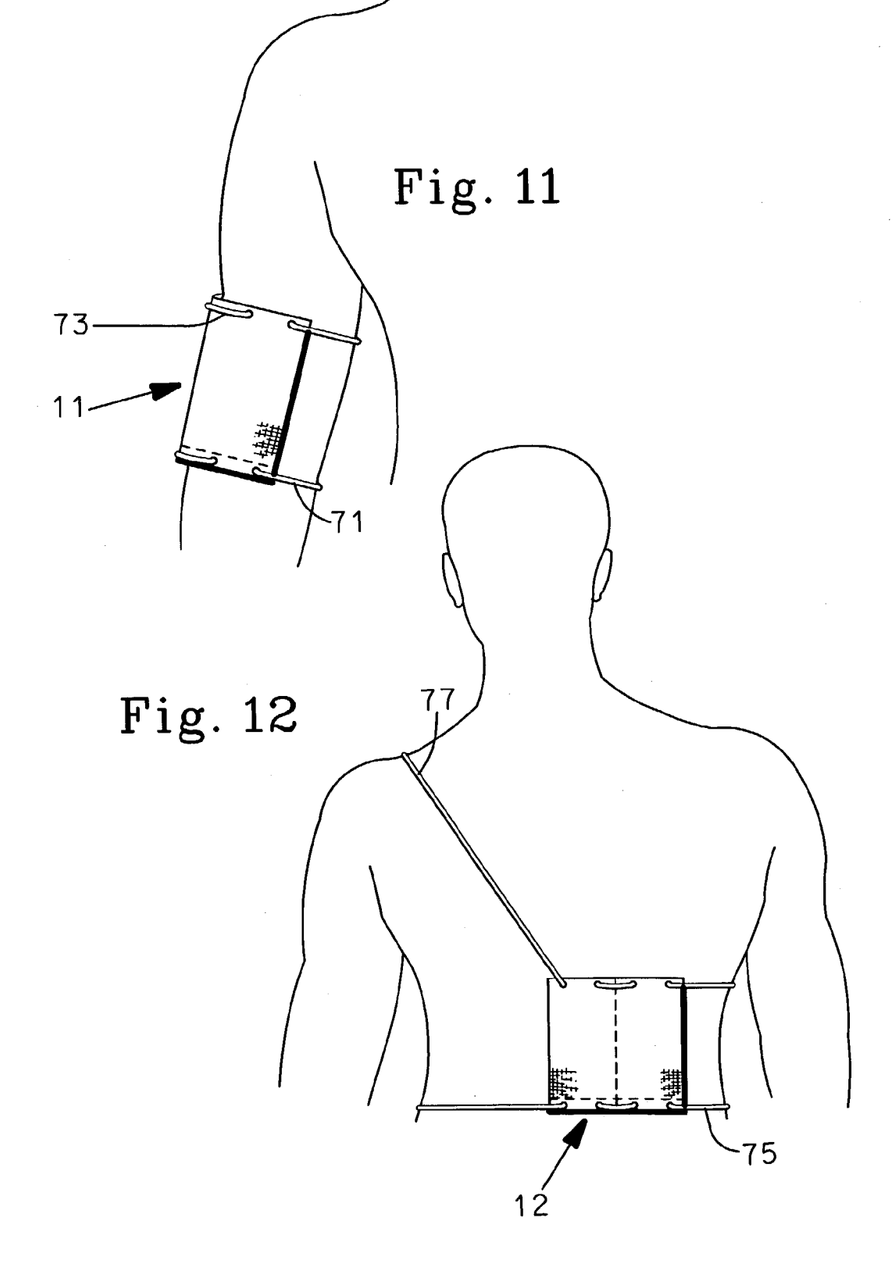
FIG. 11 shows a configuration of the ice bag device of FIG. 1 attached to a limb of a user.
FIG. 12 shows a configuration of the ice bag device of FIG. 4 attached to the body trunk of a user.

FIG. 1 shows the outside view of an ice bag device of the present invention designated generally as 11. The ice bag device 11 includes a flexible outer cover 13. The outer cover is joined along the periphery on three sides thereof to form a lateral bottom edge 15 and opposing vertical side edges 17, 19 which together define a cover interior 21 and open lateral top edges 23 and 25. The outer cover 13 is also provided with rows of a plurality of small apertures, including the row of apertures 31 which is parallel and close to the lateral bottom edge 15, and the row of apertures 33 which is parallel and close to the lateral top edge 23, and the row of apertures 35 which is parallel and close to the lateral top edge 25. Shoestring 71 is laced into the rows of apertures 31, and shoestring 73 is laced into the two rows of apertures 33 and 35, to provide fastening means to apply the ice bag device to a body part such as a person's limb, as is shown in FIG. 11 by tying the ends of the shoestrings 71 and 73 together (preferably 71 to 71 and 73 to 73, but optionally, other combinations of ends can be tied together), as well as providing the means to close the top opening that is formed by the top edges 23 and 25. The hardened and narrow tips 72a and 72b of shoestring 71 help in facilitating the lacing of said shoestring 71 through the row of apertures 31, and the hardened and narrow tips 74a and 74b of shoestring 73 help in facilitating the lacing of said shoestring 73 through the pair of row of apertures 33 and row of apertures 35. Optionally, but preferably, in order to provide a smooth bottom of the interior 21, a sewn line or glue line or a staple line is stitched or formed along line 47 on top of and close to the row of apertures 31. This stitching also strengthens the bottom edge and the apertures 31 to better receive the shoelace 71 and to sustain the weight of the ice bag device which contains a plastic zipper container filled with ice chips. Similarly, the top edges 23 and 25 are preferably strengthened by hems to better support the apertures 33 and 35, and to sustain the weight of the ice bag device. FIG. 1 also has a portion of the cover cut away to show the water-impermeable plastic inner zipper container 51 which is filled with ice chips 81.

FIG. 2 is a plan view of the isolated zipper bag container 51 which is filled with ice chips 81, and is to be placed in the cover interior 21. The inner container 51 is joined along the periphery on three sides thereof to form a bottom edge 52 and opposing side edges 53, 54 which together define a container interior and a mouth opening 55 which is sealed by the sealing strips 59.

FIG. 3 shows the cross-sectional view of ice bag device 11 comprising the outer cover 13 and the inner plastic zipper container 51 which is filled with ice chips 81. This cross-sectional view also shows the cover interior 21, the open lateral top edges 23 and 25, the lateral bottom edge 15, and the stitched line 47. The inner container 51 has a mouth opening 55 provided with a pair of sealing strips 59a and 59b. One of the sealing strips 59a, 59b is provided with a protruding rib and the other of these sealing strips is provided with a mating groove for receiving the rib in press-fit fashion to form a watertight seal. The sealing strips 59a and 59b are sealed tightly together once the inner container 51 is filled with ice chips 81. The inner container 51 useful in the present invention can be the standard size reclosable plastic sandwich bag, snack bag, or freezer bag, such as the commercially available Ziploc bags, or bag of special sizes designed especially for some ice bag devices of the present invention.

Figure 4:
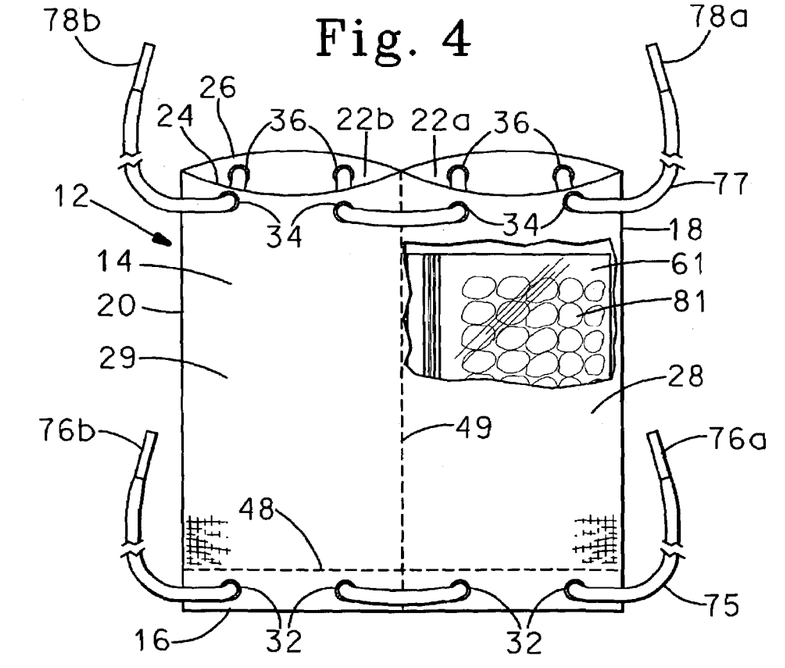
FIG. 4 is a perspective view of an alternative embodiment of the ice bag device of the present invention showing an outer cover with two vertical compartments containing two plastic zipper bags filled with ice, said outer cover is partly cut away to show one inner plastic zipper bag, and with a pair of shoestrings laced in the rows of small apertures on the lateral top and bottom sides of the outer cover.

FIG. 4 shows the outside view of an alternative embodiment of the ice bag device with two vertical compartments of the present invention designated generally as 12. The ice bag device 12 includes a flexible outer cover 14. Similar to the outer cover 13 of FIG. 1, the outer cover 14 is joined along the periphery on three sides thereof to form a lateral bottom edge 16 and opposing vertical side edges 18 and 20 which together define the cover interiors 22a and 22b, and open top edges 24 and 26. The outer cover 14 is separated into two compartments 28 and 29 of approximately equal size by a sewn line, glue line or staple line that is stitched along the vertical line 49. The outer cover 14 is also provided with rows of a plurality of small apertures, including the row of apertures 32 which is parallel and close to the lateral bottom edge 16, and the row of apertures 34 which is parallel and close to the lateral top edge 24, and the row of apertures 36 which is parallel and close to the lateral top edge 26. Shoestring 75 is laced into the row of apertures 32, and shoestring 77 is laced into the two rows of apertures 34 and 36, to provide fastening means to applied the ice bag device to a body part such as a person's body trunk, as is shown in FIG. 12, as well as providing the means to close the opening top that is formed by the top edges 24 and 26. Shoestring 75 has hardened and narrow tips 76a and 76b, and shoestring 77 has hardened and narrow tips 78a and 78b. Optionally, but preferably, in order to provide smooth interiors 22a and 22b, a sewn line or glue line is provided along line 48 above the row of apertures 32. FIG. 4 also has a portion of the cover cut away to show the water-impermeable inner plastic zipper container 61 which is filled with ice chips 81. Hidden is the inner plastic zipper container 63 which is placed in compartment 29 of the outer cover 14.

Figure 5:
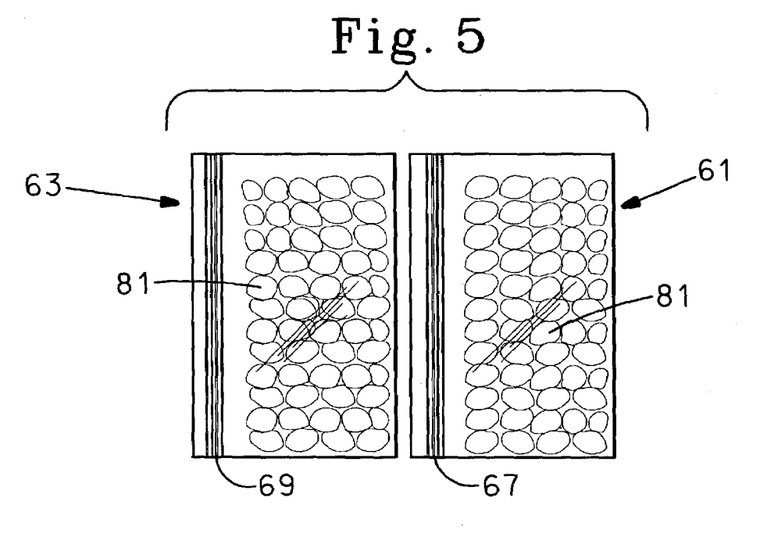
FIG. 5 is a plan view of the two zipper bags filled with ice chips of the ice bag device of FIG. 4.

FIG. 5 is a plan view of the two isolated zipper containers 61 and 63 of the ice bag device 12 of FIG. 4, with reclosable, interlocking rib and groove sealing closure 67 and 69, respectively, and filled with ice chips 81.

Figure 6:
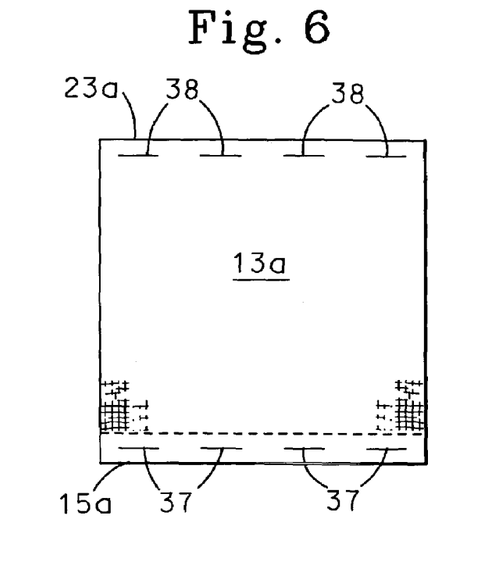
FIG. 6 is a plan view of an alternative embodiment of the outer cover of the present invention showing two rows of four small apertures each in the form of small incisions, at the lateral top and bottom sides of the outer cover.

FIG. 6 is a plan view of an alternative embodiment of the outer cover 13a of the present invention showing the row of four small apertures 37 at the bottom side 15a of the outer cover, and the row of four small apertures 38 at the top side 23a of the outer cover, wherein each aperture is in the form of a small incision.

Figure 7:
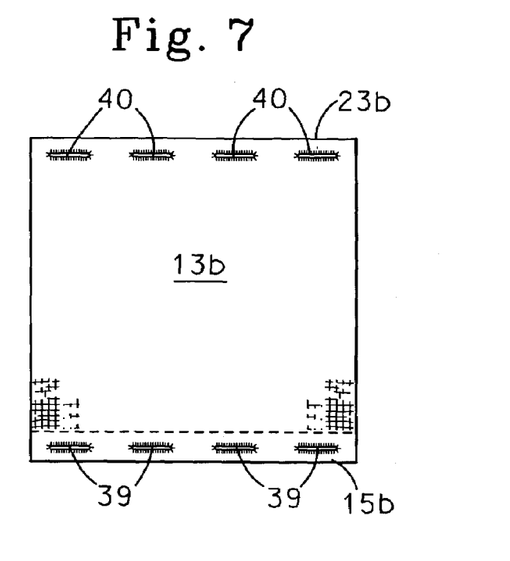
FIG. 7 is a plan view of another alternative embodiment of the outer cover of the present invention showing two rows of four small apertures each in the form of small buttonholes, at the lateral top and bottom sides of the outer cover.

FIG. 7 is a plan view of an alternative embodiment of the outer cover 13b of the present invention showing the row of four small apertures 39 at the bottom side 15b of the outer cover, and the row of four small apertures 40 at the top side 23b of the outer cover, wherein each aperture is in the form of a small buttonhole.

Figure 8:
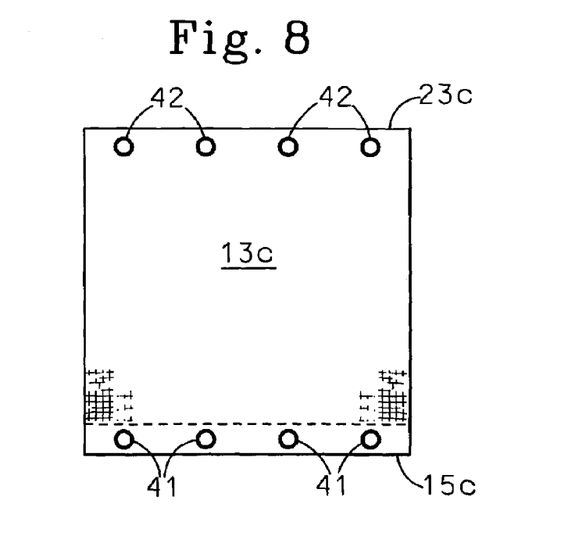
FIG. 8 is a plan view of yet another alternative embodiment of the outer cover of the present invention showing two rows of four small apertures each in the form of small metallic eyelets, at the lateral top and bottom sides of the outer cover.

FIG. 8 is a plan view of an alternative embodiment of the outer cover 13c of the present invention showing the row of four small apertures 41 at the bottom side 15c of the outer cover, and the row of four small apertures 42 at the top side 23c of the outer cover, where each aperture is in the form of a small metallic eyelet.

Figure 9:
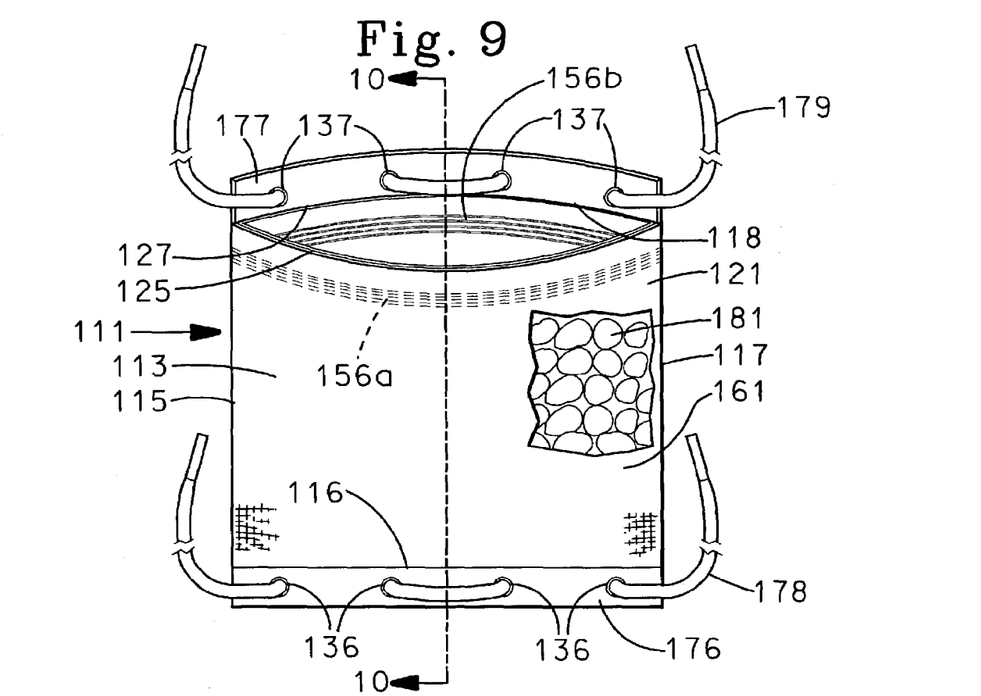
FIG. 9 is a perspective view of an alternative embodiment of the ice bag device of the present invention showing a liquid impermeable outer cover with a unitary structure to contain ice, in an open position, wherein the outer cover layer and the inner container layer are laminated together, said cover having a sack structure with three closed sides and one open side, wherein the open side is sealable by a leak-proof zipper closure to retain the ice, and with two shoestrings laced in the two rows of small apertures located in the peripheries that are extended from the open side and the closed side opposite to the open side, said outer cover is partly cut away to show the contained ice.
Figure 10:
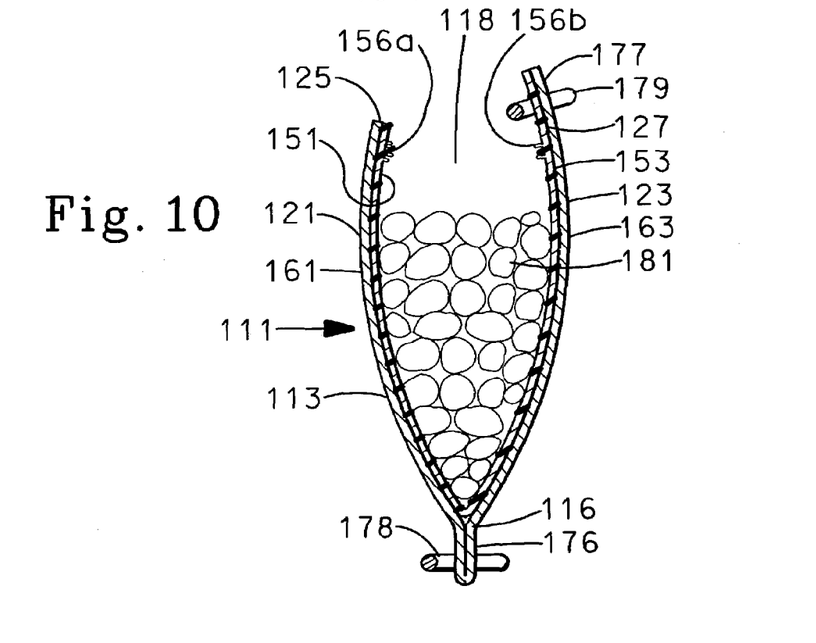
FIG. 10 is a side, cross-sectional view of the ice bag device of FIG. 9 comprising the laminated outer cover containing ice taken along the line 10—10.

FIGS. 9 and 10 are two views of an alternative embodiment of the ice bag device of the present invention, designated as 111, comprising the outer cover 113 in the open position containing ice 181. FIG. 9 is a perspective view of ice bag device 111. FIG. 10 is a cross-sectional view of the ice bag device 111 taken along the line 10—10. The liquid impermeable outer cover 113 has a sack structure with two sides 121 and 123 that are joined by three closed edges 115, 116, and 117, and one open side 118 with two edges 125 and 127. The outer cover 113 also has an extended periphery 176 which is an extension of the closed edge 116 and extended periphery 177 which is an extension of the open edge 127. The extended periphery 176 is provided with the row of small apertures 136, and the extended periphery 177 is provided with the row of small apertures 137. Side 121 comprises a water-impermeable plastic inner layer 151 which is laminated with an outer layer 161, and side 123 comprises a water-impermeable plastic inner layer 153 which is laminated with an outer layer 163. The inner layers 151 and 153 are provided with a pair of sealing strips 156a and 156b which are parallel and close to the top edges 125 and 127. One of the sealing strips 156a, 156b is provided with a protruding rib and the other of these sealing strips is provided with a mating groove for receiving the rib in press-fit fashion to form a watertight seal. The sealing strips 156a and 156b are sealed tightly together once the outer cover 113 is filled with ice 181 that is shown through a portion of the cover that is cut away in FIG. 9. The outer layers 161 and 163 are preferably made of sheet materials which can control the heat transfer, such as fabric or foam, in order to control the cooling rate, to avoid damage by overcooling, e.g., frostbite. Shoestring 178 is laced into the rows of apertures 136, and shoestring 179 is laced into the rows of apertures 137, to provide fastening means to apply the ice bag device to a body part such as a person's limb.

FIG. 11 shows the ice bag device 11 of FIG. 1 attached to a limb of a user by tying the ends of the shoelaces together.

FIG. 12 shows the ice bag device 12 of FIG. 4 attached to a body trunk of a user. FIG. 11 and FIG. 12 show preferred ways to attach the ice bag device to a body part wherein the shoelaces wrap over the vertical edges of the ice bag device in order to maximize the contact of the ice bag device to the skin.

In general, it is important to promptly treat any trauma that damages the body so as to minimize the damage. Injuries like bruises, strains, etc., can be treated by the application of cold to minimize the damage. It is therefore useful to provide a means of treating such injuries promptly with cold.

In order to provide such means, one can either provide: (1) an ice bag device comprising a flexible outer cover preferably being a unitary structure, typically either a sack structure (or pouch structure) with one open end or side, or a generally tubular structure with two open ends, with said open ends or sides optionally capable of being sealed, and having dimensions suitable to contain a cooling medium (when the cover is liquid impermeable), or one or more inner cooling packs or inner "cooling bags", hereinafter simply "pack" or "packs", wherein each said cooling pack can comprise a generally liquid impermeable container containing cooling media that can be inserted into said outer cover through said open end, and wherein said outer cover has a plurality of small apertures, wherein "plurality" is typically from 1 to about 40, preferably from about 2 to about 20, and more preferably from about 4 to about 10 small apertures, to permit the insertion of one, or more separate, string-like, members that can be used to attach the ice bag device, when it is assembled and filled with at least one cooling pack, to an injured body part of the user; and optionally, but preferably, to permit lacing one of the string-like members through the small apertures in both sides of the bag near each open end of the outer cover to close said open end; (2) a non-constrictive ice bag device comprising a flexible outer cover for a cooling medium, having a layer of mounting adhesive to temporarily attach said cover, when it is filled with the cooling medium (when the cover is liquid impermeable) or one or more inner "cooling bags", or inner cooling packs, containing the cooling medium, to the inside or the outside of a garment, such that said cooling medium is in close contact with an injured body part of a user, without the need for a strapping and/or wrapping means, wherein the flexible outer cover is preferably a unitary structure, typically either a sack structure (or pouch structure) with one open end to receive one or more inner cooling packs, wherein each cooling pack comprises either a resealable or a sealed fluid impermeable, preferably plastic, container containing a cooling medium, or a closed sack structure containing one or more inner cooling packs, wherein each cooling pack comprises a permanently sealed fluid impermeable plastic container containing a cooling medium (In a preferred embodiment, the outer cover is self-adhering with the adhesive layer being an integral part of the outer cover and entirely or partially covering one side of the outer cover. In another preferred embodiment, the outer cover is not self-adhering, but with the adhesive layer being separated from the outer cover and being in the form of one or more adhesive strips, such as bandage adhesive strips or adhesive bandage strips, that are used to attach the outer cover to the garment. The adhesive layer is optionally, but preferably, covered with a release paper layer to protect the adhesive from prematurely sticking to a surface other than the intended user's garment.); and/or (3) a non-constrictive ice bag device comprising a flexible ice bag outer cover which is filled with a cooling medium (when the cover is liquid impermeable) or at least one inner "cooling bag", or inner cooling pack, containing cooling medium, preferably said outer cover having an extended periphery on at least one side to permit attaching said outer cover, when it is assembled and filled with the cooling medium or at least one cooling pack containing cooling medium, to the inside or the outside of a garment using a plurality of safety pins, wherein "plurality" is typically from 1 to about 20 safety pins, such that said cooling medium is in close contact with an injured body part of an individual, without the need for a strapping and/or wrapping means, wherein said outer cover typically comprises a piece of flexible substrate, such as a piece of fabric, more preferably said outer cover being a sack structure (or pouch structure) with one or more open ends (or sides) and having two or more extended peripheries (or extended sides, or extended edges) that have a width of at least about 0.5 centimeter, more preferably of at least about 1 centimeter, and wherein said cooling medium is contained in either a resealable or sealed, typically flexible, typically plastic, liquid impermeable inner container to form an inner cooling pack, wherein said cooling medium is preferably either ice, ice and water combination, refrigeratable cooling gel, or endothermic chemical cooling system, wherein said inner cooling pack can be inserted through said open end(s) and/or side(s) of said outer cover, and wherein said open end(s) and/or side(s) are capable of being sealed to retain the said inner cooling pack using the said safety pins or the outer cover is sealable or sealed and comprises a liquid impermeable layer and the cooling media is inside the outer cover.

The above covers are normally used to contain one or more inner cooling bags or packs containing a cooling medium. Each inner cooling pack comprises either a resealable or permanently sealed fluid impermeable plastic container containing a cooling medium, preferably either ice, water, ice and water combination, refrigeratable cooling gel, or endothermic chemical cooling mixture. However, if the outer cover is closed, it can contain one or more inner cooling packs, wherein each cooling pack comprises a permanently sealed fluid impermeable plastic container containing a cooling medium, preferably either refrigeratable cooling gel or endothermic chemical cooling mixture.

The above ice bag devices and covers can be used in methods in which first aid treatment of injuries is achieved by attaching the outer covers hereinabove holding one or more inner fluid impermeable plastic containers containing a cooling medium to an injured part, preferably by attachment to a garment so as to apply said cooling medium to an injured body part when the garment is worn. The covers are used in creating a non-constrictive ice bag device, preferably by providing said outer covers, filling one or more plastic zipper containers sealable by interlocking rib and groove sealing closure, with ice or an ice and water combination, placing the filled container(s) inside said outer covers, using an adhesive layer, safety pins, and/or string-like members to attach the assembled ice bag device to the injured part, preferably by attaching the cover inside or outside of a garment, such that said ice bag device is in close contact with an injured body part of the user. The inner cooling pack can comprise a resealable zipper container containing ice and/or an endothermic chemical system pack or a permanently sealed cooling pack containing ice or cooling gel, when such cooling pack is available.

It is important for first aid purposes to associate the covers, etc., with instructions for use to ensure that the method can be practiced efficiently, quickly, and effectively so as to maximize the effect of the cooling treatment on an injury. Preferably, the various parts are combined in an article of manufacture comprising the outer cover(s), optionally, one or more resealable or permanently sealed liquid impermeable containers for the cooling media, optionally, a sealed plastic wrapper to keep the outer cover and the optional elements in a hygienic, non-contaminated condition in storage, and preferably instructions for use. The article can also comprise string-like members and/or safety pins, and/or adhesive strips for purposes of attaching the cover(s) to a garment or a body part.

If string-like members are to be used for attachment of the ice bag device, it is important to provide some small aperture(s) through which the string-like member can be threaded before tying the string-like member around the body part or forming a loop for attachment. Similarly, safety pins or adhesive layer can be used to attach an ice bag device to a garment such that said ice bag device is in close contact with an injured body part of an individual when the garment is worn, and/or to close the opening of the outer cover of said ice bag device, but it is important to have a periphery which can be penetrated by the pins without puncturing the bag containing the cooling media. Combinations of these attachment means can be used.

The cover(s) and the ice bag(s) are preferably compact, not bulky, preferably washable, and are optionally disposable.

The above description discloses, by way of example, some preferred embodiments of the present invention. However, persons of ordinary skill in the art are capable of creating numerous modifications within the scope of the claims. Changes in specifics of form and details can be made to the above-described embodiments. The claims and not the examples are the measure of the protected invention.

What is claimed is:

1. A flexible outer cover for an ice bag device having an open end that is optionally capable of being sealed, and having dimensions suitable to contain one or more cooling packs and/or alternatively a cooling medium when the cover is generally liquid impermeable, wherein each said cooling pack comprises a separate generally liquid impermeable container containing cooling media, that can be inserted through said open end, and wherein said outer cover has a plurality of small apertures to permit the insertion of one, or more separate string-like members that can be used to attach the ice bag device, when it is assembled and filled with at least one cooling pack or a cooling medium, to an injured body part of a user.

2. The outer cover of claim 1 wherein said cover has a sac like structure having a generally rectangular or square configuration when flattened, said cover having small apertures in both edges of said open end to permit lacing a string-like member through said apertures to close said open end, and to permit the attachment of the assembled ice bag device to said injured body part.

3. The outer cover of claim 2 wherein said cover has one or more compartment(s) to hold a corresponding number of cooling pack(s) wherein each said cooling pack comprises an inner plastic container having a rib and groove sealing closure and containing ice or an ice and water combination, and wherein each row of apertures of the outer cover has from about 2 to about 10 apertures which are either small incisions, eyelets, buttonholes, or combinations thereof.

4. The outer cover of claim 3 wherein either: said cover has one compartment to hold one said cooling pack; said container is a commercially available food or freezer zipper bag; or said cover has one compartment to hold one said cooling pack and said container is a commercially available food or freezer zipper bag.

5. The outer cover of claim 2 wherein either: each said row of apertures has from about 4 to about 6 small apertures; each said string-like member is made of either natural and/or synthetic fibers, fabric, leather, or combinations thereof; or each said row of apertures has from about 4 to about 6 small apertures and each said string-like member is made of either natural and/or synthetic fibers, fabric, leather, or combinations thereof.

6. The outer cover of claim 2 wherein each said string-like member is either a shoelace or shoestring, a bootlace, or a draw cord, and, optionally, wherein said string-like member has a length of from about 0.5 meter to about 1.5 meter.

7. The outer cover of claim 1 wherein said cover is made of material which is either woven, knitted, crocheted, non-woven fabric of natural and/or synthetic fibers, felt, velvet, flocked material, heat-bonded plastic fiber material, solvent-laid thermally bonded plastic fiber material, open-cell plastic foam, close-cell plastic foam, porous plastic film, nonporous plastic film, rubber, paper, laminated materials, or combinations thereof.

8. The outer cover of claim 2 wherein each said cooling pack comprises a permanently sealed fluid impermeable plastic container containing a cooling medium selected from the group consisting of at least partially frozen liquid, cooling gel, or endothermic chemical cooling system.

9. The outer cover of claim 1 wherein the outer cover layer and the inner container layer are laminated together, said cover having a sack structure with three closed sides and one open side, wherein the open side is sealable by a leak-proof zipper closure to contain ice, and wherein the open side and the closed side opposite to the open side have extended peripheries having rows of small apertures that permit string-like members to be threaded through to attach the ice-filled cover to an injured body part of the user, and wherein the wall of the cover is preferably made of laminates of plastic and woven or non-woven fabric layers.

10. An ice bag device comprising:
    (a) a flexible outer cover according to claim 1;
    (b) at least one plastic liquid impermeable inner container suitable for holding a cooling medium to form a cooling pack, wherein said inner container either is completely sealed and contains a cooling gel, frozen water, or an endothermic chemical cooling system, or has one open side that can be closed by means of a resealable zipper closure and contains ice or an ice and water mixture, and wherein said cooling packs have dimensions that enable them to fit inside the outer cover; and
    (c) one or more string-like members.

11. The ice bag device of claim 10 wherein either: said inner container is a commercially available zipper bag containing ice or an ice and water combination; said outer cover comprises two string-like members each of which is either a loose shoelace or shoestring, a loose bootlace, or a draw cord; or said inner container is a commercially available zipper bag containing ice or an ice and water combination and said outer cover comprises two string-like members each of which is either a loose shoelace or shoestring, a loose bootlace, or a draw cord.

12. A method of creating an ice bag device by the step of filling one or more plastic zipper containers with ice or an ice and water combination; placing the filled container(s) inside an outer cover of claim 1; and using loose shoelaces or bootlaces to attach the completed ice bag device to the an injured body part, and optionally to close the end of said outer cover.

13. A method of using shoelaces or bootlaces to attach to an injured member of a human or animal an ice bag device having a cover that has a series of small apertures, to a body part, and/or to close an opening of the cover of said ice bag device by lacing said shoelaces or bootlaces through said apertures and then optionally tying the ends of said shoelaces or bootlaces to attach said ice bag device to said injured member.

14. An article of manufacture comprising the following elements: one or more flexible outer covers according to claim 1; optionally one or more empty zipper containers, or one or more sealed fluid impermeable containers containing water, cooling gel, or endothermic chemical cooling system; optionally two or more shoelaces; and optionally a sealed plastic film wrapper to contain one or more of said elements; and optionally packaged in association with a set of instructions for use that tells an individual one or more of: how to use the cover to assemble an ice bag device; how to use the product properly; what benefits can be achieved; and how best to obtain these benefits, wherein said set of instructions is in one or more languages, and wherein said set of instructions is in words, in illustrative images and/or icons, or words in combination with illustrative images and/or icons.

15. The article of claim 14 comprising either: one or more outer covers, one or more empty zipper containers, optionally a pair of shoelaces, and optionally a sealed plastic film wrapper; or one outer cover having one or more compartments, the corresponding number of empty zipper containers to be placed in the compartment(s) of the outer cover, optionally a pair of shoelaces, and optionally a sealed plastic film wrapper.

16. The article of claim 14 packaged in association with a set of instructions comprising the steps to take in using one said outer cover to assemble an ice bag device, said steps including:
    a. filling one or more plastic zipper containers with ice or other cooling medium;
    b. placing the filled container(s) inside the compartment(s) of the cover;
    c. using laces from footwear to lace through the apertures in the cover and to seal the open end(s) of the cover; and
    d. using the laces to attach the assembled ice bag device to an injured body part of an injured person;
and, optionally, wherein the set of instructions also comprises one or more of:
    (1) the instruction to direct the consumer to a source of ice cubes or ice chips, including a home refrigerator, ice boxes for beverages at a sport game, and/or at a fast food restaurant and/or a hotel or motel on a trip;
    (2) the instruction to direct the consumer to use already cooled gel packs in the place of the ice-filled inner bags;
    (3) the instruction to direct the consumer to use endothermic chemical cooling packs in the place of the ice-filled inner bags;
    (4) the instruction to direct the consumer to tie two or more short shoelaces together to form a longer string for a large body part, when long shoelaces are not available; and/or
    (5) the instruction to direct the consumer to keep said article in their first-aid kit.

17. The article of claim 15 comprising a pair of shoelaces having a length of from about 0.25 meter to about 2 meter and having narrow and hardened tips.

18. The article of claim 15 comprising a pair of short shoelaces having a length of from about 0.3 meter to about 0.6 meter, and wherein the set of instructions comprises the instruction to direct the consumer to use a pair of longer shoelaces that are removed from a pair shoes to tie the assembled ice bag device to the injured body part, and use the pair of short shoelaces that are provided for temporarily tying the shoes.

19. The article of claim 14 wherein the set of instructions is printed on one or more of: the package, the wrapper, and/or an accompanying instruction flyer or booklet; and/or is communicated via print and/or electronic mass media, optionally selected from newspapers, magazines, radio, television, internet, circulars to members of sport and/or outdoor organizations, and combinations thereof.

20. The method of doing business wherein the article of claim 14 is distributed with the approval of one or more entities having an association with individuals that are likely to be injured and need an ice bag device on an urgent basis, said entity optionally being an amateur or professional athletic association and/or optionally, attaching the indicia of at least one of said entities to said article and/or associating said indicia with said article.

* * * * *